Nov. 16, 1965 J. M. GARABEDIAN Plant Pat. 2,575
PLUM TREE
Filed May 11, 1964
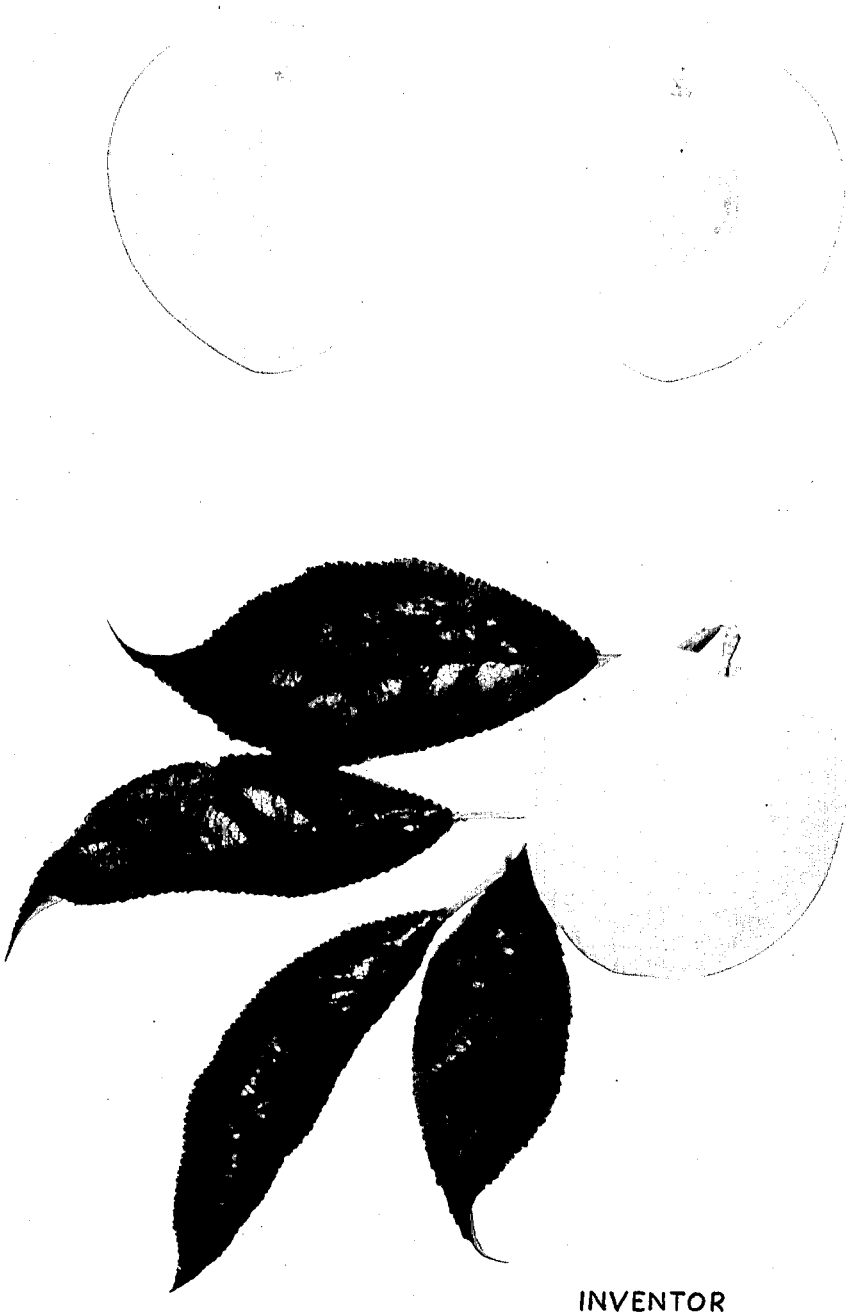
INVENTOR
*John M. Garabedian*
*Webster & Webster*
ATTYS.

United States Patent Office

Plant Pat. 2,575
Patented Nov. 16, 1965

2,575
PLUM TREE

John M. Garabedian, Fresno, Calif., assignor to Peach & Willow Farms, Fresno, Calif., a corporation of California Filed May 11, 1964, Ser. No. 366,671
1 Claim. (Cl. Plt.—38)

This present invention relates to a new and distinct variety of plum tree of the Japanese type; such variety having been originated by me in a test or experimental orchard located near Fresno, county of Fresno, State of California, as an open pollinated seedling of the Santa Rosa (unpatented). More particularly, the present variety of plum tree is a selection from a number of such open pollinated Santa Rosa seedlings, and one which evidenced certain novel and commercially desirable characteristics over the Santa Rosa.

Subsequent to its origination, the herein claimed variety was asexually reproduced, under my control and direction, by budding on mature cut back trees in the test orchard heretofore mentioned. Under careful observation, I ascertained that such asexual reproductions ran true to the original tree in all respects.

In comparison to the Santa Rosa—which it most nearly resembles—the present variety of plum tree is particularly characterized, as to novelty:

By a heavy crop of fruit, and which fruit is exceptionally large for the season of maturity;

By fruit which is very firm and hangs well on the tree so that such fruit can be marketed over a relatievly long period of time;

By fruit having superior shipping quality;

By fruit having good eating quality—the fruit although acid in early stages of maturity, having an excellent acid-sugar balance after a few days in storage; and By fruit which has a yellow ground color substantially overspread with bright red; there being a distinct bloom on the fruit. The Santa Rosa, on the other hand, turns a very dark red and softens quickly, lacking the bright red and firm flesh of the instant variety.

The drawing is an illustration, by photographic reproduction in color, of a twig with leaves, a whole fruit, and another fruit cut in half with the halves disposed to expose the flesh.

Referring now more specifically to the pomological details of this new and distinct variety of plum tree, the following is an outline description thereof; all major color plate identifications being by reference to the Nickerson Color Fan (developed by the United States Department of Agriculture), except where common terms of color definition are employed.

Tree:

*Size.*—Medium.
*Vigor.*—Medium.
*Growth.*—Spreading.
*Density.*—Medium.
*Form.*—Vase-shaped.
*Hardiness.*—Hardy, in California.
*Production.*—Very productive.

Trunk:

*Size.*—Medium.
*Texture.*—Medium.

Branches:

*Size.*—Medium.
*Texture.*—Medium.
*Color.*—Brown.
*Lenticels.*—Number—medium. Size—medium.

Leaves:

*Size.*—Average length—2¾". Average width—1¾".
*Form.*—Elongated — ovate. Acuminate; acutely painted.
*Thickness.*—Medium.
*Texture.*—Smooth—tends to be wavy toward margin, giving irregular appearance.
*Margin.*—Finely serrate.
*Petiole.*—Medium length; medium thickness.
*Glands.*—Average number—3. Alternate; small globose; brown; positioned on petiole at base of blade.
*Stipules.*—Wanting.
*Color.*—Dark green.

Flower buds:

*Hardiness.*—Hardy.
*Size.*—Medium.
*Length.*—Medium.

Flowers:

*Blooming period.*—Average date of first bloom—February 25th. Average date of full bloom—March 5th. Medium as compared with other varieties.
*Size.*—Medium.
*Color.*—White.

Fruit:

*Maturity when described.*—Eating ripe—July 6th.
*Average date of first picking.*—June 25th.
*Average date of last picking.*—July15th.
*Size.*—Uniform; large. Average diameter axially—2⅛" to 2⅝". Average transversely in suture plane—2¼" to 2¾".
*Form.*—Uniform; globose to round; slightly compressed on ventral suture toward apex.
*Suture.*—An inconspicuous line; extends from base to apex.
*Ventral surface.*—Rounded.
*Cavity.*—Flaring; circular. Average depth—¼". Average breadth—¼".
*Base.*—Rounded.
*Apex.*—Rounded.
*Pistil point.*—Rounded.

Skin:

*Thickness.*—Thick.
*Texture.*—Medium.
*Flavor.*—Slightly astringent.
*Tenacity.*—Tenacious to flesh.
*Tendency to crack.*—None in dry season.
*Color.*—Greenish-yellow (10Y 9/9) substantially overspread with red (7.5 R 6/12)to (5R 5/13), shading darker to (2.5R 3/7) in later stages of maturity.

Flesh:

*Amygdalin.*—Moderate.
*Juice.*—Abundant.
*Texture.*—Firm; meaty.
*Fibers.*—Few; medium.
*Ripens.*—Evenly.
*Flavor.*—Slightly acid, with good sugar balance.
*Aroma.*—Distinct.
*Eating quality.*—Good.
*Color.*—Yellow (5Y 9/9), mottled with red next to skin on sunny side; the red increasing in the flesh as fruit matures. *Surface of pit cavity*—yellow.

Stone:

*Type.*—Cling; adheres to flesh over entire surface.
*Fibers.*—Short.
*Size.*—Medium. Average length—1$\frac{1}{16}$". Average breadth—⅝". Average thickness—¼".
*Form.*—Ovoid.
*Hilum.*—Narrow.
*Apex.*—Acute; very sharp narrow point about ⅛" in length.
*Sides.*—Flattened.

*Surface.*—Pitted throughout, with shallow furrow near ventral edge. Some stones rough and irregular especially on dorsal edge.

*Pits.*—Irregular.

*Ventral edge.*—Thick.

*Dorsal edge.*—Narrow, with narrow groove from base to center.

*Ridges.*—Interrupted on dorsal edge, continuous on ventral edge.

*Tendency to split.*—Slight.

*Color.*—Strong brown (5YR 4/5).

Use: Market; dessert.

Keeping quality: Good.

Shipping quality: Good.

The tree and its fruit herein described may vary in slight detail due to climatic and soil conditions under which the variety may be grown; the present description being of the variety as grown in the Central Valley of California.

The following is claimed:

A new and distinct variety of plum tree, substantially as illustrated and described, characterized—in comparison to the Santa Rosa—by the bearing of a heavy crop of clingstone fruit, and which fruit is exceptionally large for the season of maturity; by fruit which is firm and hangs well on the tree; by fruit having superior shipping quality and good eating quality; and by fruit having cream-yellow flesh, and yellow skin substantially overspread with bright red and with a distinct bloom.

No references cited.

ABRAHAM G. STONE, *Primary Examiner.*